(12) United States Patent
Kim et al.

(10) Patent No.: US 9,012,179 B2
(45) Date of Patent: Apr. 21, 2015

(54) METHOD FOR MASS-PRODUCING ANTIFREEZE PROTEIN DERIVED FROM POLAR YEAST

(75) Inventors: Hakjun Kim, Incheon (KR); Sungho Kang, Seoul (KR); Junhyuck Lee, Incheon (KR); Sunggu Lee, Incheon (KR); Sejong Han, Gyeonggi-do (KR); Jongchan Park, Busan (KR); Kyoungsun Park, Gwangju (KR)

(73) Assignee: Korea Ocean Research and Development Institute, Ansan-Si, Gyeonggi-do (KR)

( * ) Notice: Subject to any disclaimer, the term of this patent is extended or adjusted under 35 U.S.C. 154(b) by 25 days.

(21) Appl. No.: 14/117,225

(22) PCT Filed: May 17, 2011

(86) PCT No.: PCT/KR2011/003647
§ 371 (c)(1),
(2), (4) Date: Mar. 12, 2014

(87) PCT Pub. No.: WO2012/157794
PCT Pub. Date: Nov. 22, 2012

(65) Prior Publication Data
US 2014/0193854 A1     Jul. 10, 2014

(30) Foreign Application Priority Data
May 13, 2011 (KR) .................. 10-2011-0044852

(51) Int. Cl.
*C12P 21/02* (2006.01)
*C07K 14/39* (2006.01)
*C12N 15/81* (2006.01)

(52) U.S. Cl.
CPC .............. *C07K 14/39* (2013.01); *C12N 15/815* (2013.01)

(58) Field of Classification Search
None
See application file for complete search history.

(56) References Cited

PUBLICATIONS

Davies, P. L. and Sykes, B. D., Curr. Opin. Struct. Biol. 7, pp. 828-834 (1997).
Davies, P. L. et al., Philos Trans R Soc Lond B Biol Sci. 357, pp. 927-935 (2002).
3. D'Amico, S. et al., EMBO Rep.7, pp. 385-389 (2006).
4. Jia, Z. And Davies P.L., Trends Biochem. Sci. 27, pp. 101-106 (2002).

*Primary Examiner* — Jim Ketter
(74) *Attorney, Agent, or Firm* — Weisun Rao; Greenberg Traurig, LLP

(57) ABSTRACT

The present invention relates to a method for mass-producing an antifreeze protein derived from a polar yeast, and more particularly, to a method for mass-producing an antifreeze protein derived from *Leucosporidium* sp., which is the polar yeast, for synthesizing a recombinant polynucleotide by optimizing and altering a gene, which codes the antifreeze protein derived from the polar yeast, for a yeast expression system, and for expressing same using the yeast expression system.

4 Claims, 14 Drawing Sheets

```
        10          20          30          40          50          60
MSLLSIITIG  LAGLGGLVNG  QRDLSVELGV  ASNFAILAKA  GISSVPDSAI  LGDIGVSPAA
        70          80          90         100         110         120
ATYITGFGLT  QDSSTTYATS  PQVTGLIYAA  DYSTPTPNYL  AAAVANAETA  YNQAAGFVDP
       130         140         150         160         170         180
DFLELGAGEL  RDQTLVPGLY  KWTSSVSVPT  DLTPEGNGDA  TWVFQIAGGL  SLADGVAFTL
       190         200         210         220         230         240
AGGANSTNIA  FQVGDDVTVG  KGAHFEGVLL  AKRFVTLQTG  SSLNGRVLSQ  TEVALQKATV
       250         260
NSPFVPAPEV  VQKRSNARQW  L
```

Fig. 2

```
SEQUENCE LISTING

<160> NUMBER OF SEQ ID NOS: 1

<210> SEQ ID NO 1
<211> LENGTH: 726
<212> TYPE: DNA
<213> ORGANISM: Artificial Sequence
<220> FEATURE:
<223> OTHER INFORMATION: Modified sequence of Leucosporidium sp. AY30

<400> SEQUENCE: 1
cagagagact tgtctgttga attgggtgta gccagcaact ttgccatctt ggcaaaagca      60
ggtatttcgt cagttccaga ttccgcaatc ttaggagata tcggtgttag tccagccgct     120
gccacttata ttaccggatt cggacttact caagactcat ccactacata tgccacttct     180
cctcaagtga ccggtttaat ctacgcagct gattactcta ctccaacacc aaattacttg     240
gcagctgctg ttgccaacgc tgagacggct tacaatcagg ccgcaggatt cgtcgaccca     300
gacttcttgg agctaggagc aggagaattg cgtgaccaga ctttggttcc aggtctgtac     360
aagtggacgt cttccgtaag tgttcctacc gacctcactt ttgaaggtaa cggtgacgct     420
acatgggttt ttcaaattgc cggaggattg tccttggctg atggtgttgc ttttaccttg     480
gcaggcggag ctaactccac taacatcgct ttccaagtgg gagacgacgt tactgtcgga     540
aagggtgctc attttgaagg ggtcctactt gcaaagcgtt tcgtgacatt acaaactgga     600
tctagtttga atggaagggt gctgtctcaa acagaagtag cattacaaaa agcaacagtt     660
aattcaccat ttgttccagc tcccgaggtt gttcagaaaa gaagtaatgc cagacagtgg     720
ttgtaa                                                                 726
```

METHOD FOR MASS-PRODUCING ANTIFREEZE PROTEIN DERIVED FROM POLAR YEAST

CROSS-REFERENCE TO RELATED APPLICATIONS

This application is a National Phase application of International Application No. PCT/KR2011/003647 filed May 17, 2011, which claims priority to Korean Patent Application No. 10-2011-0044852 filed May 13, 2011, the contents of both of which applications are incorporated by reference herein in their entirety.

TECHNICAL FIELD

The present invention relates to a method for mass-producing an antifreeze protein derived from arctic yeast and, more particularly, the present invention relates to a method for mass-producing an antifreeze protein by synthesizing a recombinant polynucleotide, modified by optimizing a gene coding an antifreeze protein derived from arctic yeast, *Leucosporidium* sp., and expressing the recombinant polynucleotide in a yeast expression system.

BACKGROUND ART

Polar organisms should overcome the problems of decreased enzyme activity, decreased membrane fluidity, inactivation and improper folding of proteins, formation of intracellular ice crystals, etc. to survive in low-temperature, polar environments. Among others, the formation of ice crystals causes physical damages and dehydration of tissues due to the growth of ice crystals, thus causing serious damage to polar organisms. Polar organisms produce various antifreeze proteins (hereinafter referred to as "AFPs") to survive at low temperatures. AFPs inhibit the growth of ice crystals in vivo and the recrystallization of ice to protect polar organisms from sub-zero temperatures to survive (Davies, P. L. and Sykes, B. D., *Curr. Opin. Struct. Biol.* 7, 1997, 828-834; Davies, P. L. et al., Philos Trans R Soc Lond B Biol Sci. 357, 2002, 927-935; D'Amico, S. et al., EMBO Rep. 7, 2006, 385-389).

AFPs are proteins that generally have a flat ice-binding surface and bind to specific surfaces of ice crystals, thus inhibiting the growth of ice crystals and the recrystallization of ice. AFPs create a difference between the melting point and freezing point. This is called thermal hysteresis (TH), which can be measured using a nanoliter osmometer and used as an indicator of AFP activity. Moreover, AFPs do not lower the freezing point in proportion to the concentration, unlike typical antifreeze used in vehicles. That is, AFPs can effectively lower the freezing point even at very low concentrations by direct interaction with ice, thus minimizing damage due to osmotic pressure generated in vivo during freezing (Jia, Z. and Davies P. L., *Trends Biochem. Sci.* 27, 2002, 101-106).

The unique features of AFPs that prevent the growth of ice crystals and inhibit the recrystallization of ice have been used in various commercial fields. For example, in the agricultural field, AFP expression in plants has been attempted for the purpose of preventing cold-weather damage to plants. Moreover, in the field of fisheries, there has been an attempt to produce a transgenic fish by expressing AFPs in commercially available fish such as Atlantic salmon (*Salmo salar*) or goldfish (*Carassius auratus*) so as to enable farming in cold areas. Furthermore, in the medical field, research on the use of AFPs in cryosurgery and as an additive in cryopreservation of blood, stem cells, umbilical cord blood, organs, and germ cells has continued to progress. In addition, in the food field, AFPs are also used in product production for frozen storage of smoother ice scream. In the field of cosmetics, functional cosmetics containing AFPs for preventing frostbite have already been sold. Although AFPs are widely used in various commercial fields as mentioned above, there are still limitations in mass production of recombinant AFPs due to low-level expression of AFPs and folding problems. This is mainly because most AFPs have disulfide bonds and are stabilized by disulfide bonds, which thus makes it difficult to express recombinant proteins and yields improper folding of expressed proteins.

Since AFPs were first discovered in fish living in cold water, various types of new AFPs have been discovered in insects, plants, fungi, microorganisms, etc. New AY30 AFP derived from arctic yeast, *Leucosporidium* sp., has recently been recovered. The AY30 AFP has no cysteine amino acid residues, and thus during production of recombinant proteins, the level of protein expression is high, and the folding problem due to improperly formed disulfide bonds does not occur, As a result, the AY30 AFP is suitable for mass production of recombinant AFPs.

Therefore, the present inventors have synthesized a recombinant polynucleotide by modifying an AFP gene to be expressed using codon optimization for a yeast expression system and inserted the recombinant polynucleotide into a yeast-derived expression vector so as to mass-produce an antifreeze protein (AFP) derived from arctic yeast by overexpressing AFP in the form of activated protein. As a result, the present inventors have obtained a large amount of AFP and found that the AFP is glycosylated, thus completing the present invention. All references cited in this specification are hereby incorporated by reference in their entirety.

DISCLOSURE

Technical Problem

An object of the present invention is to provide a method for mass-producing an industrially useful activated AFP.

Technical Solution

To achieve the above object, the present invention provides a method for mass-producing an antifreeze protein (AFP) by synthesizing a recombinant polynucleotide, modified by optimizing a gene coding an antifreeze protein derived from arctic yeast, *Leucosporidium* sp., and expressing the recombinant polynucleotide in a yeast expression system.

Advantageous Effects

According to the method for producing a recombinant AY30 AFP of the present invention, AFPs having an activity similar to that of native AFP can be mass-produced, and the recombinant AY30 AFP or a culture medium containing the same can be effectively used as an anti-icing additive in various fields such as medical, military, frozen food, cold weather damage prevention plant storage, etc.

DESCRIPTION OF DRAWINGS

FIG. 2 shows the DNA sequence of antifreeze protein of *Leucosporidium* sp. AY30 and the alignment of recombinant polynucleotide sequence (Syn_AY30) obtained by codon optimization according to the present invention.

FIGS. 3 and 4 are graphs showing the amount of cultured cells obtained by culturing a transformant according to the present invention, in which FIG. 3 shows the optical density with the lapse of culture time, and FIG. 4 shows the dry cell weight (DCW) with the lapse of culture time.

FIGS. 6 to 8 are images showing the comparison of expression patterns of recombinant AY30 AFP according to the culture temperature, in which FIG. 6 shows the expression pattern at 30° C., FIG. 7 shows the expression pattern at 25° C., and FIG. 8 shows the expression pattern at 20° C.

FIGS. 12 and 13 are images showing that the recombinant AY30 AFP according to the present invention inhibits the growth of ice crystals, measured with a nanoliter osmometer, in which FIG. 12 shows recombinant the AY30 AFP cultured at 30° C. and FIG. 13 shows the recombinant AY30 AFP cultured at 25° C.

MODE FOR INVENTION

Hereinafter, the present invention will be described in detail.

The present invention provides a method for mass-producing an AY30 AFP derived from arctic yeast, *Leucosporidium* sp., or a culture medium containing the same, the method comprising the steps of: (1) synthesizing a recombinant polynucleotide modified by optimizing a gene coding an AY30 AFP derived from arctic yeast, *Leucosporidium* sp.; (2) introducing the recombinant polynucleotide of step (1) into a yeast-derived expression vector; (3) culturing a transformant containing the recombinant expression vector; and (4) obtaining a culture medium from step (3).

Here, the information on the DNA sequence coding the AY30 AFP derived from arctic yeast, *Leucosporidium* sp., in step (1) is found in Swiss-Prot/TrEMBL (accession number: C7F6X3), and the polynucleotide comprising the nucleotide sequence of SEQ. ID. No.: 1 expressed using codon optimization for a yeast expression system is synthesized using the same.

When the polynucleotide comprising the nucleotide sequence of SEQ. ID. No.: 1 is expressed in eukaryotic cells, in particular in yeast, it produces a glycosylated protein, thus obtaining an activated AY30 AFP.

Moreover, although the yeast-derived expression vector in step (2) may include any yeast-derived expression vectors known in the art, the yeast-derived expression vector may preferably be a *Pichia pastoris*-derived expression vector, most preferably pPICZαA in the present invention.

Figure 1:
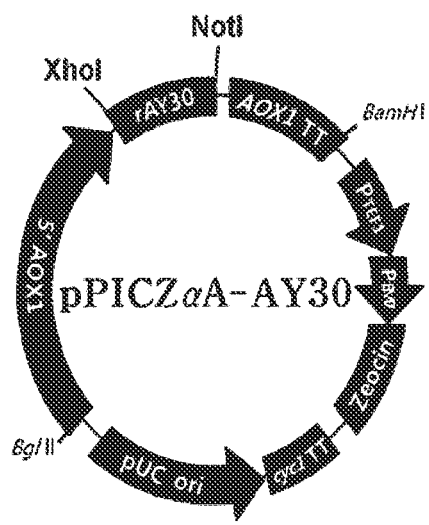
FIG. 1 shows a restriction enzyme map of a recombinant vector expressing a recombinant antifreeze protein derived from arctic yeast according to the present invention.

Specifically, pPICZαA induces the expression of AY30 AFP using an alcohol oxidase promoter (AOX) and has a signal sequence, α-factor mating signal sequence, which induces secretion in a culture medium such that the signal sequence is attached to the N-terminal during the expression of the recombinant polynucleotide, thus allowing the recombinant AFP to be secreted in the culture medium (see FIG. 1).

In the present invention, the polynucleotide comprising the nucleotide sequence of SEQ. ID. No.: 1 is inserted into pPIC-ZαA to produce a recombinant expression vector, pPICZαA-AY30, which has been deposited as follows:

Name of Depositary institution: Korea Research Institute of Bioscience and Biotechnology Accession No.: KCTC 11917BP Date of Deposit: Apr. 15, 2011. All restrictions imposed by the depositor on the availability to the public of the deposited material will be irrevocably removed upon the granting of the patent.

Then, a recombinant AY30 AFP is obtained by culturing a yeast transformant transformed with the recombinant expression vector, pPICZαA-AY30. Here, *Pichia pastoris* may preferably be used as the host yeast. Specifically, a transformant, *P. pastoris* X33/Mut$^+$/pPICZαA-AY30, transformed from *Pichia pastoris* X33 with pPICZαA-AY30 is provided. The transformation of host cells may be performed by methods known in the art to which the present invention pertains, and preferably performed by electroporation in the present invention.

The culturing of the transformant may be performed by yeast culture known in the art to which the present invention pertains.

In the present invention, first, the transformant is grown in quantity, and then the expression of the recombinant AY30 AFP is induced.

First, for the mass growth of the transformant, a culture medium obtained from seed culture is used as the seed for fermentation to perform the cell culture.

Specifically, it is preferable that the seed culture is incubated by shaking in YPD medium and the fermentation is performed in a medium containing nutrients such as glycerol, PTM1 Trace Salts, etc. for mass propagation of the transformant.

It is preferable that the culture temperature is maintained in a range of 15° C. to 35° C., and the maximum growth of the culture is obtained at a culture temperature of 20° C. or higher.

Next, the transformant, *P. pastoris* X33/Mut$^+$/pPICZαA-AY30, according to the present invention triggers the expression of the recombinant AY30 AFP by methanol, and thus the expression of AFP is induced in methanol fed-batch culture.

That is, the supply of glycerol, a nutrient used in the fermentation, is terminated, and methanol is supplied when the glycerol is exhausted to increase the level of dissolved oxygen, thus inducing the expression of the recombinant AY30 AFP. The induction of expression is performed in a manner that the supply of methanol is stopped when the level of dissolved oxygen is less than 20% and the methanol is resupplied when the level of dissolved oxygen increases.

The recombinant AY30 AFP according to the present invention is extracellularly secreted by a signal sequence at the N-terminal and thus can be continuously cultured without disrupting the transformant, which makes it possible to continuously obtain a culture medium containing the recombinant AY30 AFP.

Moreover, the present invention provides a method for preventing freezing of a sample at a predetermined temperature by adding to the sample a culture medium containing the transformant, *P. pastoris* X33/Mut+/pPICZαA-AY30, or the recombinant AY30 AFP isolated therefrom.

Here, the predetermined temperature refers to a temperature that is 0 to 10° C. lower than the freezing point of the sample or a solution for storing the sample. The freezing of the sample is effectively prevented at temperatures 0 to 4° C. lower. At these temperatures, the recrystallization of ice is prevented by the recombinant AY30 AFP, thus preventing the freezing of the sample and sample storage liquid.

The sample includes frozen foods, medicines, agricultural chemicals, pigments, biological materials, etc.

Here, the frozen foods include all frozen or cold stored foods such as ice cream, frozen fruits, frozen meat, etc., which are required to be stored at low temperatures.

Specifically, in frozen desserts such as ice cream, frozen yogurt, ice blended, slurry, etc., the AFPs prevents the generation of large crystals due to the recrystallization of ice at temperatures below the freezing point of the sample and maintains the fine structure of ice crystals on frozen food, thus improving the taste and quality of frozen food.

Moreover, in frozen or cold stored foods such as frozen fruits, frozen vegetables, frozen meat, etc., the AFPs prevents significant damage to the taste and quality of food taken in a frozen state or after thawing, which is caused when the original state of the food is destroyed by the generation of large crystals due to the recrystallization of ice during food freezing.

In biological materials such as therapeutic drugs, mammalian cells for plasma and tissue culture, etc. the freezing and thawing process significantly reduces the cell viability, and the freezing of tissue for organ transplant causes serious damage to the functions of living cell. Moreover, the cold-weather damage to plants causes serious problems in agriculture, and when the drugs are not stored under strict temperature conditions, the efficacy of the drugs may be destroyed or the drugs may be dangerous. In this case, the AFPs allow the biological materials to resist sudden changes in temperature by inhibiting the recrystallization of ice.

Hereinafter, the present invention will be described with reference to Examples. However, the following examples are intended to illustrate the present invention, and the present invention is not limited by the following Examples.

Example 1

Synthesis of Recombinant Polynucleotide and Production of Transformant 1-1. Synthesis of Recombinant Polynucleotide The arctic yeast used in the present invention was *Leucosporidium* sp. AY30, which was isolated by Korea Ocean Polar Research Institute (KOPRI) from the Tvillingbenet Lake in the Arctic Svalbard archipelago.

Codon optimization of *Pichia* was performed on AY30 gene to increase the expression of the recombinant AY30 AFP in *Pichia pastoris* using complete gene sequences of AY30 AFP (Swiss-Prot/TrEMBL accession number: C7F6X3). Artificial gene synthesis is a method of artificially synthesizing genes without any template DNA, and double-strand DNA with desired length was produced by bonding of chemically synthesized oligonucleotides based on their sequence homology. Specifically, artificial genes were synthesized by overlap extension PCR, and the basic synthesis procedures used were design and synthesis of oligonucleotides, overlap extension PCR, and cloning and sequencing.

As a result, the sequence of a recombinant polynucleotide comprising the nucleotide sequence of SEQ. ID. NO: 1 was produced.

Figure 2:
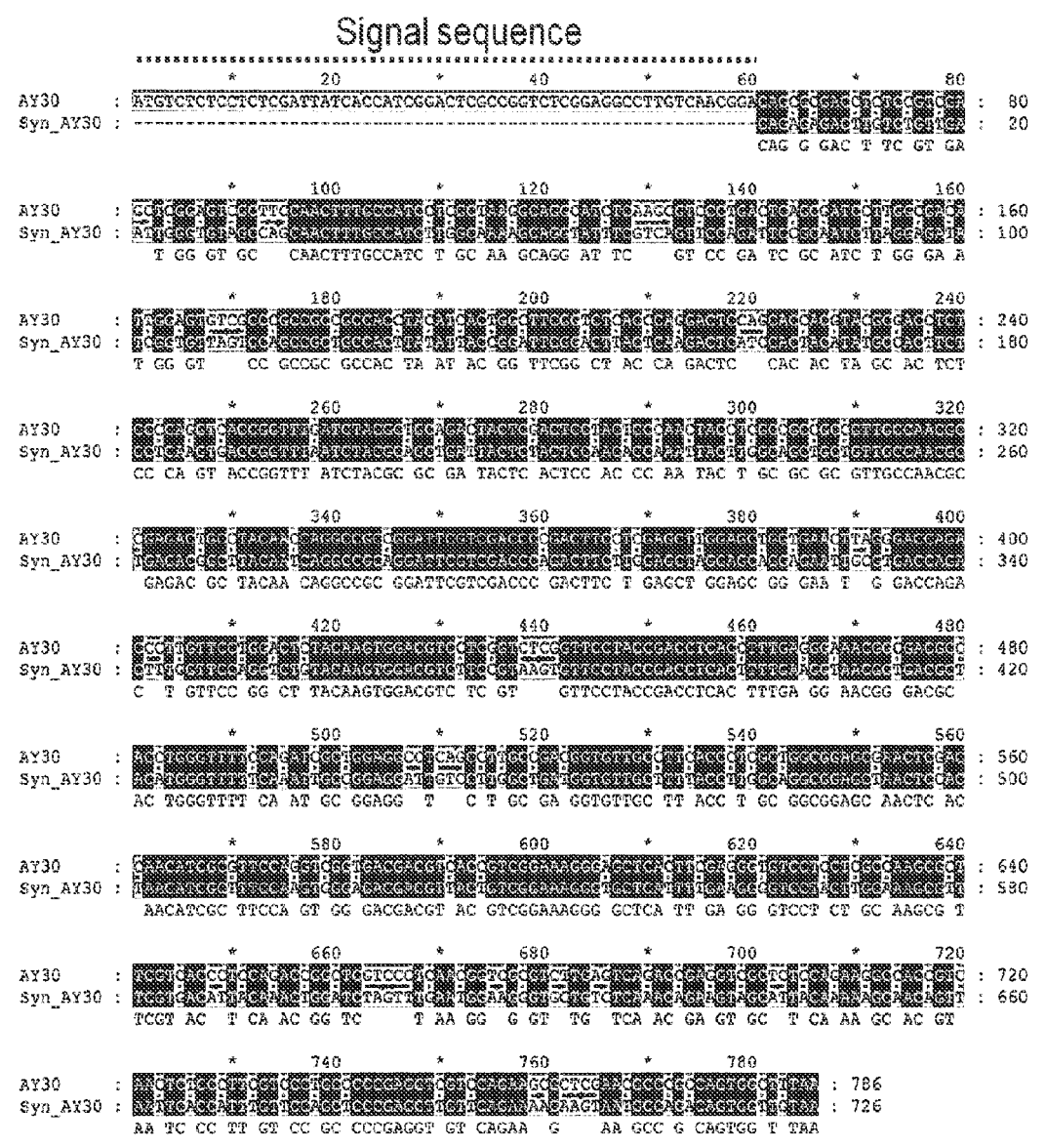

The DNA sequence of AY30 AFP (Swiss-Prot/TrEMBL accession number: C7F6X3) and the alignment of DNA sequence (Syn_AY30) obtained by codon optimization for the expression of the recombinant protein are shown in FIG. 2.

1-2. Production of Recombinant Expression Vector

*Pichia pastoris* (Invitrogen, San Diego, Calif.) is a methylotrophic yeast strain X33, and AFP AY30 was mass-produced using an alcohol oxidase promoter (AOX1) of a recombinant *P. pastoris* X33/Mut+ (methanol utilization plus) strain.

The recombinant polynucleotide sequence synthesized in 1-1 was inserted at a restriction enzyme of pPICZαA using the alcohol oxidase promoter (AOX1) to produce a recombinant expression vector pPICZαA-AY30.

This recombinant expression vector has been deposited in the Biological Resource Center, Korea Research Institute of Bioscience and Biotechnology (Accession No.: KCTC 11917BP) on Apr. 15, 2011.

1-3. Production of Transformant

Electroporation was used to transform *P. pastoris* X33/Mut+ with the recombinant expression vector pPICZαA-AY30.

Plasmid DNA containing AY30 AFP inserted into pPICZαA was treated with the restriction enzyme Sac I to prepare a linear plasmid that could be inserted into the genomic DAN of the strain.

*P. pastoris* X33/Mut+ strain for the transformation was inoculated into YPD and incubated at 30° C. and 200 rpm for 18 hours, and then cells were isolated by centrifugation (5000 rpm, 25° C., 2 min). The isolated strain was resuspended in ice-cold DW and 1M sorbitol and then centrifuged twice, respectively.

3 μg plasmid DNA was added to the prepared cells and incubated on ice for 10 minutes. The DNA/cell suspension was transferred to a pre-cooled 0.1 cm electroporation cuvette, electroporated with a pulse (capacitance of 25 μF, voltage of 900 V), and then immediately transferred on ice. Ice-cold 1M sorbitol was added and then placed in a culture tube, and the resulting mixture was incubated at 30° C. and 200 rpm for 1 hour together with YPD. YPD solid medium was incubated at 30° C. for 3 days.

Transformant *P. pastoris* X33/Mut+/pPICZαA-AY30 was obtained by the above process.

Example 2

Culture of Yeast Strain 2-1. Seed Culture

*Leucosporidium* sp. AY30 was incubated in NB medium (5 g/l peptone, 3 g/l beef extract) at 2° C. and subjected to shaking culture for 7 days.

The seed culture of the recombinant transformant *P. pastoris* X33/Mut+/pPICZαA-AY30, in which the recombinant AY30 polynucleotide would be expressed, was incubated in YPD medium (10 g/l yeast extract, 20 g/l peptone, 20 g/l dextrose) in a shaking incubator at 30° C. and 250 rpm overnight and used as the seed for fermentation.

2.2 Fermentation Culture

Mass culture of the recombinant transformant *P. pastoris* X33/Mut+/pPICZαA-AY30 was performed using a 7 L jar bottom magnetic drive fermentor (KoBioTech, Korea) and a 500 L fermentor (KF-500 KoBioTech, Korea) with a 50 L seed fermentor. The measurement and recording of temperature was performed using a thermocouple inside a tube of the fermentor. The measurement of dissolved oxygen was performed using a sterilized, polarographic dissolved oxygen electrode InProO$_2$ Sensors (Mettler-Toledo GmbH, Switzerland).

Fermentation medium was used by adding 4.35 ml/l PTM1 Trace Salts (6 g/l cupric sulfate-5H$_2$O, 0.08 g/l sodium iodide, 3 g/l manganese sulfate-H$_2$O, 0.2 g/l sodium molybdate-2H$_2$O, 0.02 g/l boric acid, 0.5 g/l cobalt chloride, 20 g/l zinc chloride, 65 g/l ferrous sulfate-7 H$_2$O, 0.2 g/l biotin, 5 ml/l sulfuric acid) to fermentation basal salts medium (26.7 ml/l phosphoric acid 85%, 0.93 g/l calcium sulfate, 18.2 g/l potassium sulfate, 14.9 g/l magnesium sulfate-7H$_2$O, 4.13 g/l potassium hydroxide, 40 g/l glycerol). The pH was adjusted by adding acid and base using a peristaltic pump and measured using an InPro pH sensor (Mettler-Toledo GmbH, Switzerland).

Air was supplied at 30° C. and 15 L/min, and the mixture was incubated by shaking at 600 rpm, and the level of saturated dissolved oxygen was maintained 20 to 30%. The pH was maintained at pH 5 using ammonia water.

A small amount of antifoaming agent was added to the fermentation medium before inoculation of *P. pastoris* X33/Mut$^+$/pPICZαA-AY30, and bubbles generated during the incubation were removed using the antifoaming agent.

2-3. Glycerol Batch and Fed-Batch Cultures

Normal fermentation continued during the growth of cells by consuming the glycerol initially added in 2-2. The time when the level of dissolved oxygen suddenly increased was analyzed to confirm that the initial glycerol was all exhausted.

Glycerol fed-batch culture was performed to increase the cell concentration and the production of AFP. Here, 50% w/v glycerol containing 12 ml/l PTM1 trace salts was used, and the supply of glycerol was set at 18.15 ml/hr/liter in the initial fermentation medium. The supply of glycerol was performed for 9 hours until the time when the cell density was increased 3 to 4 times that before the supply of glycerol at a cell density of OD$_{600}$.

2-4. Methanol Fed-Batch Culture

To induce the expression of the recombinant AFP, the supply of glycerol was terminated, and 100% methanol containing 12 ml/l PTM1 trace salts was supplied at 3.6 ml/hr/liter in the initial fermentation medium when the glycerol was exhausted to increase the level of dissolved oxygen. Moreover, the temperature conditions were set at 30° C., 25° C., 20° C., and 15° C. The supply of methanol was stopped when the level of dissolved oxygen was less than 20% and the methanol was resupplied at the above ratio when the level of dissolved oxygen increased.

As a result, a cell culture medium containing the recombinant AFP secreted in the culture medium was obtained.

Example 3

Measurement of Cell Content

The Measurement of cell content was performed by measuring the optical density (OD) at 600 nm using a UV spectrophotometer (Ultrospec 3300 pro, Amersham Biosciences, Sweden). Each 1 mL culture medium was centrifuged, washed with 0.9% NaCl solution, and dried in a dryer at 80° C. for 48 hours, and then the dry cell weight (DCW) was measured. The correlation depending on the fermentation temperature was obtained between the OD values and the DCW values obtained after fermentation at each temperature.

Figure 3:
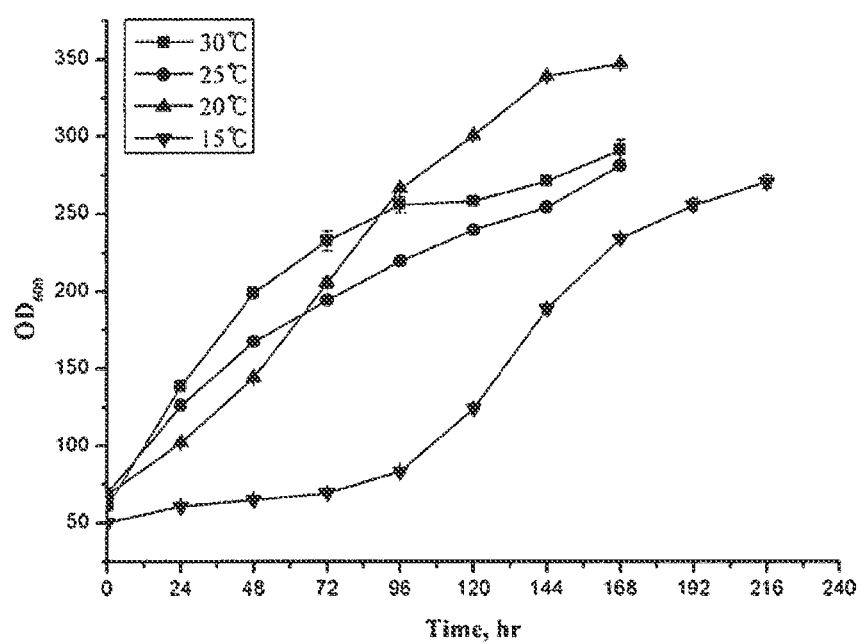
Figure 4:
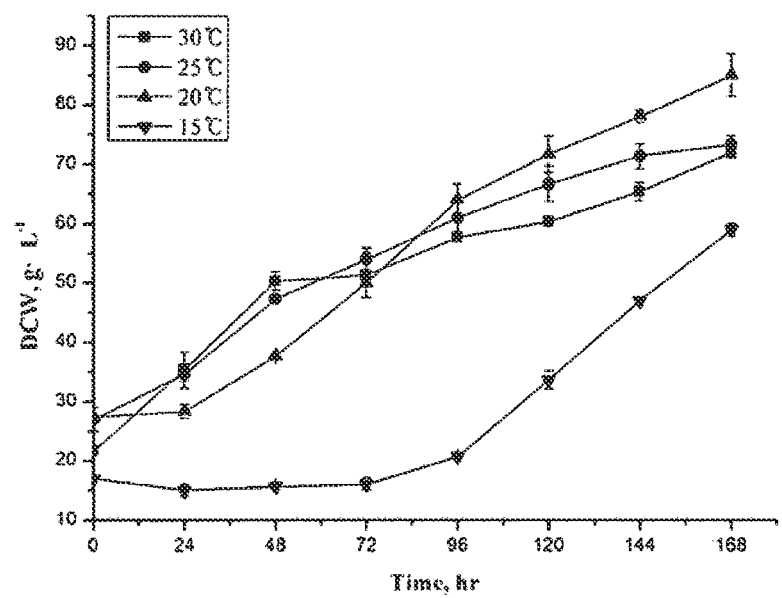

As a result, as shown in FIG. 3, the change in OD$_{600}$ with the lapse of time started similarly at the beginning and the fermentation was accelerated at 20° C. after 7 days and showed a similar tendency at 30° C. and 25° C. after 7 days. Moreover, the growth curve at 20° C. from 4 days elapsed was plotted over the growth curves at 25° C. and 30° C. Furthermore, as shown in FIG. 4, the dry cell weight (DCW) was the same as the result of OD$_{600}$, and the cell density at 20° C. was great.

Example 4

Measurement of Total Protein Content

The total protein content of the culture medium was measured by Bradford protein assay using bovine serum albumin (BSA) as standard.

Specifically, each 15 ml culture medium was collected in units of 24 hours during sample incubation, and each 1 ml was centrifuged at 4° C. and 4500 rpm for 5 min to separate cells and supernatant. Each 20 μl BSA solution diluted with 0 μg, 50 μg, 100 μg, 500 μg, 1000 μg, and 2000 μg, respectively, was mixed with 1 ml Bradford reagent (SIGMA-ALDRICH, USA), and the protein concentrations were measured at 595 nm using a UV spectrophotometer, thus establishing a correlation formula of the standard protein content. Each 20 μl sample was used by the same method as above, and the total protein content was obtained by substituting the measured values into the correlation formula of the standard protein content using BSA.

Figure 5:
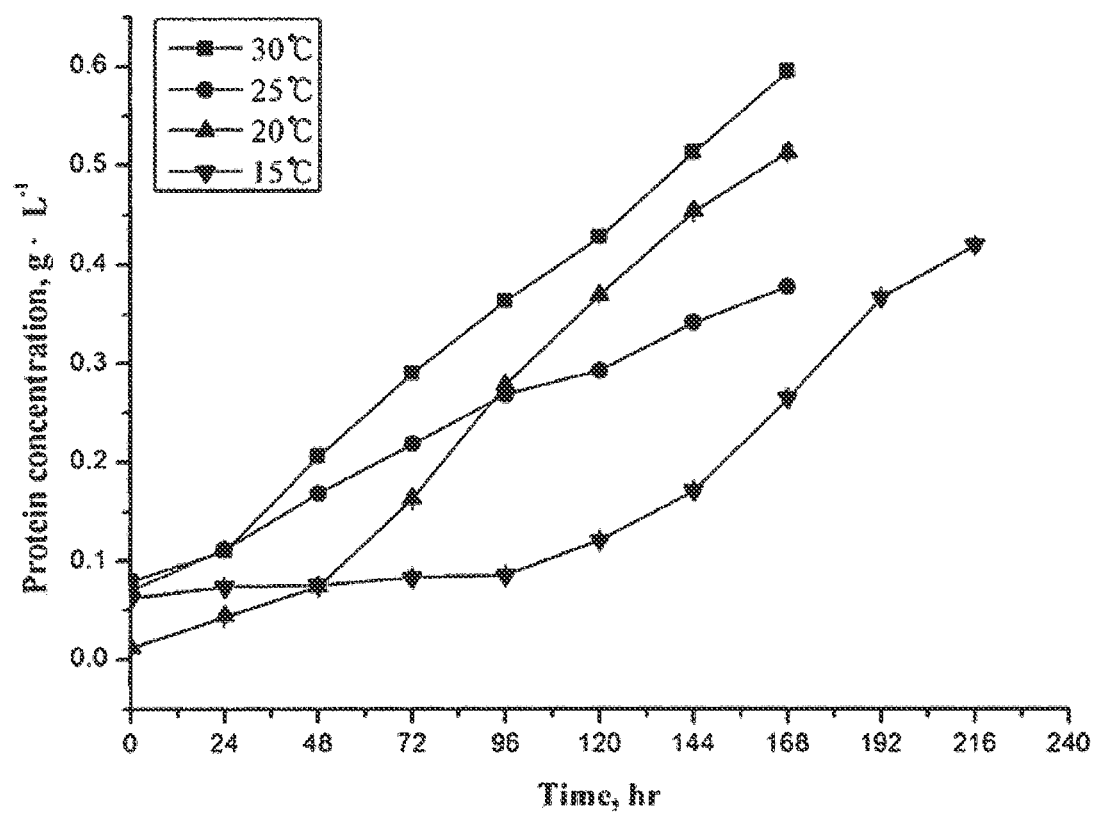
FIG. 5 is a graph showing the content of total protein in a culture medium obtained by culturing a transformant according to the present invention.

As a result, as shown in FIG. 5, the total protein content of the culture medium after culture at 30° C. was the highest.

Example 5

SDS-PAGE Analysis

Supernatants of the culture medium were collected in units of 24 hours during sample incubation and mixed with the same amount of 2× SDS gel loading buffer (126 mM Tris-Cl pH 6.8, 4% SDS, 0.02% Bromophenol Blue, 20% Glycerol, 5% β-mercaptoethanol). The resulting samples were denatured at 95° C. and analyzed by SDS-polyacrylamide gel electrophoresis (PAGE) as described by Laemmli. The SDS-PAGE analysis was performed using 1× running buffer (25 mM Tris base, 192 mM Glycine, 1% SDS), 12% separating gel (40% Acrylamide, 1.5 M Tris pH 8.8, 10% SDS, 10% APS, Temed), and stacking gel (40% Acrylamide, 1.5 M Tris pH 6.8, 10% SDS, 10% APS, Temed).

After the SDS-PAGE analysis was performed in the above manner, the gel was fixed with a fix solution (40% ethanol, 7% acetic acid), oxidized with oxidation solution (1% periodic acid, 3% acetic acid), stained with Schiff's reagent (SIGMA-ALDRICH, USA), and then reduced in a reduction solution (0.58% potassium metabisulfite, 3% acetic acid).

Figure 6:
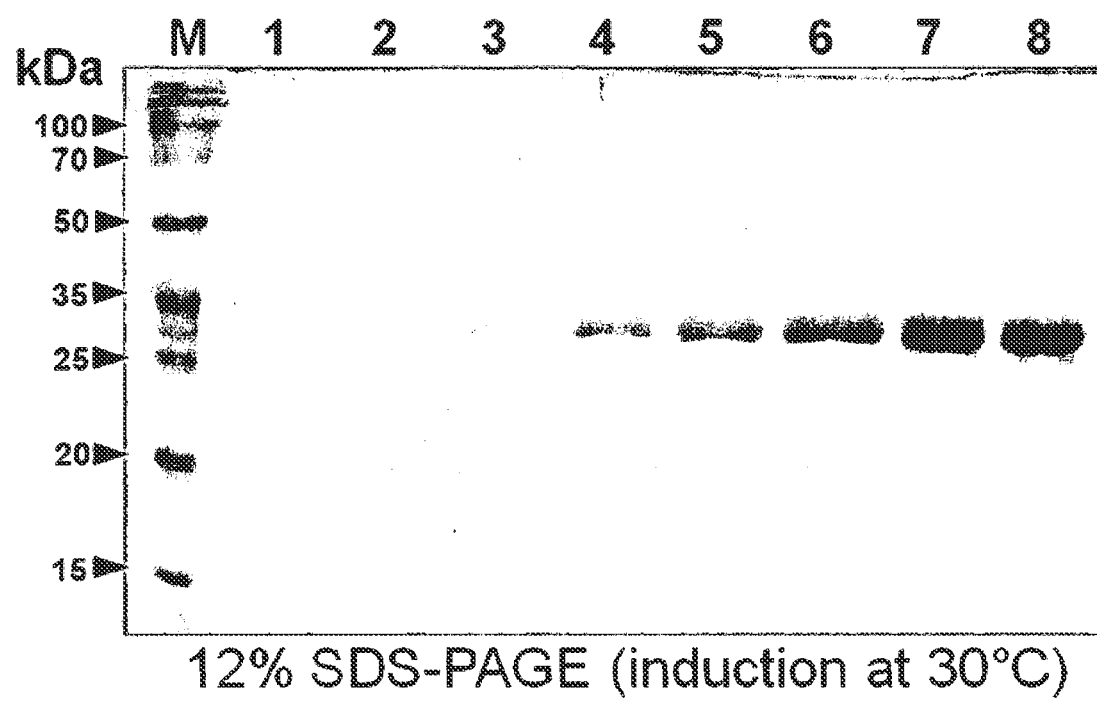
Figure 7:
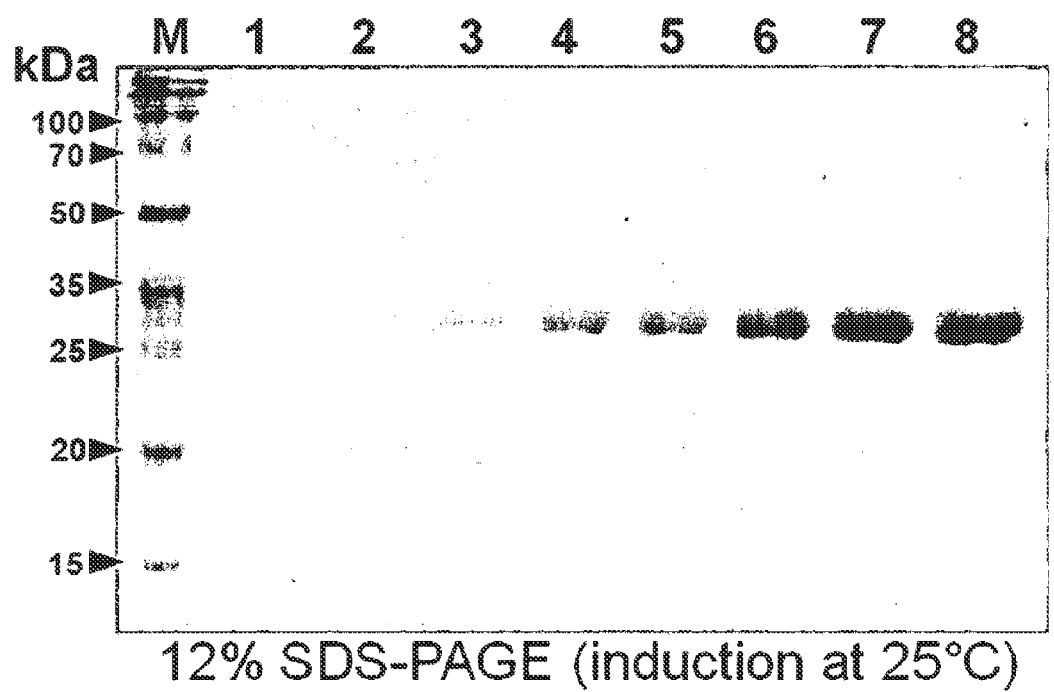
Figure 8:
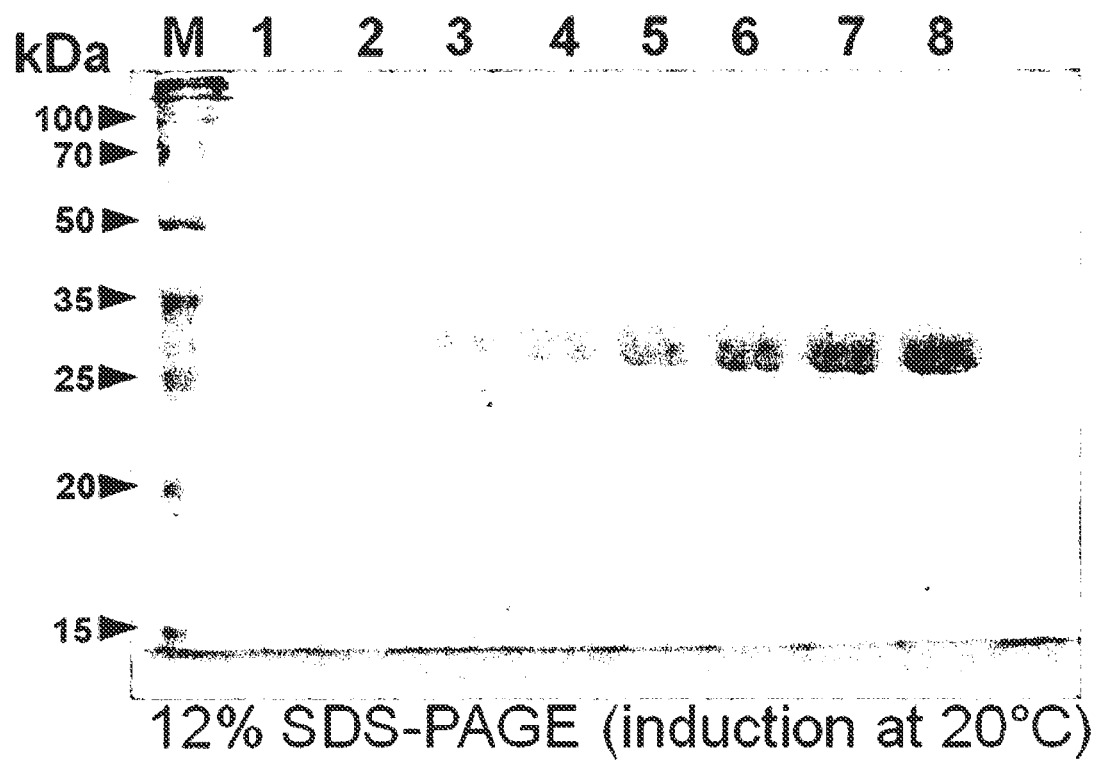

As a result, as shown in FIGS. 6 to 8, it was found that a relatively large amount of recombinant AY30 AFP was contained in the sample incubated at 30° C.

To investigate the glycosylation of the recombinant AFP, the expression of the recombinant AFP was determined by staining the samples with Coomassie brilliant blue (CBB) staining solution (0.25% Coomassie brilliant blue R250, 45% methanol, 10% glacial acetic acid), and the glycosylation of the AFP was determined using Periodic acid Schiff reagent (PAS).

Here, the recombinant AY30 AFP produced in a bacterial expression system was expressed in *E. coli* B121 (DE3) using pCold I.

Figure 9:
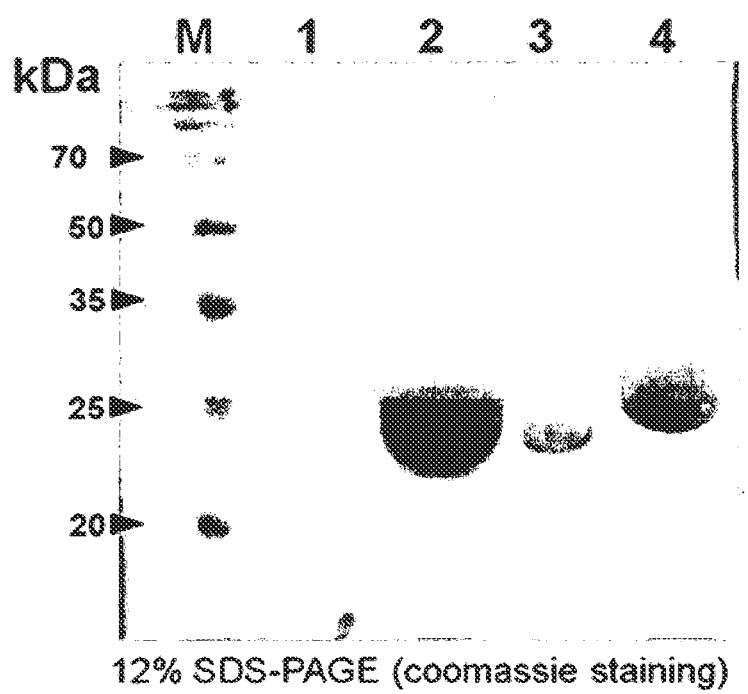
FIGS. 9 and 10 are images showing the results of glycosylation of recombinant AY30 AFP by coomassie staining and PAS staining (1: native AY30 AFP; 2 and 3: recombinant AY30 AFP produced in a bacterial expression system; and 4: recombinant AY30 AFP produced in a *Pichia pastoris* expression system).
Figure 10:
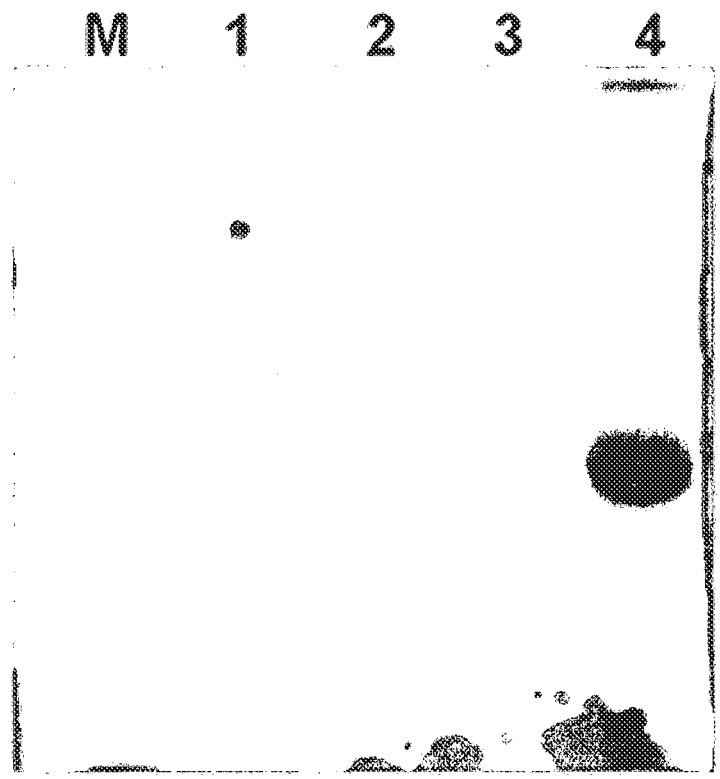

As a result, as shown in FIGS. 9 and 10, it was found that the recombinant AY30 AFP expressed in *P. pastoris* X33/Mut$^+$/pPICZαA-AY30 according to the present invention was the glycosylated active form, like the native AFP.

Example 6

Western Blot Analysis

After the SDS-PAGE analysis, the AFP on the gel was transferred to a PVDF membrane (MILLIPORE, USA) using a transfer buffer (5.1 g/l bicine, 6.55 g/l Bis-Tris, 0.375 g/l EDTA, 10% methanol, pH7.2) at 1000 mM for 1.5 hours. Then, the membrane was washed twice with TBS buffer (20 mM Tris, 140 mM NaCl, pH7.5), incubated in blocking buffer (3% bovine serum albumin, 20 mM Tris, 140 mM NaCl, pH7.5) for 1 hour, washed twice with TBSTT buffer (0.1% Tween20, 0.2% Triton X-100, 20 mM Tris, 140 mM NaCl, pH7.5), washed once with TBS buffer, and incubated in blocking buffer containing a primary antibody (1/8000 dilution) (Anti-rIAY30 poly. Ab. Rabbit, Cosmo gene Tech, Korea) for 1 hour. Then, the resulting membrane was washed twice with TBSTT buffer, washed once with TBS buffer, incubated in blocking buffer containing a secondary antibody (1/90000 dilution) (Anti-rabbit IgG, Sigma, USA) for 1 hour, washed four times with TBST buffer, and visualized with BCIP/NBT-purple Liquid Substrate System (Sigma, USA).

Figure 11:
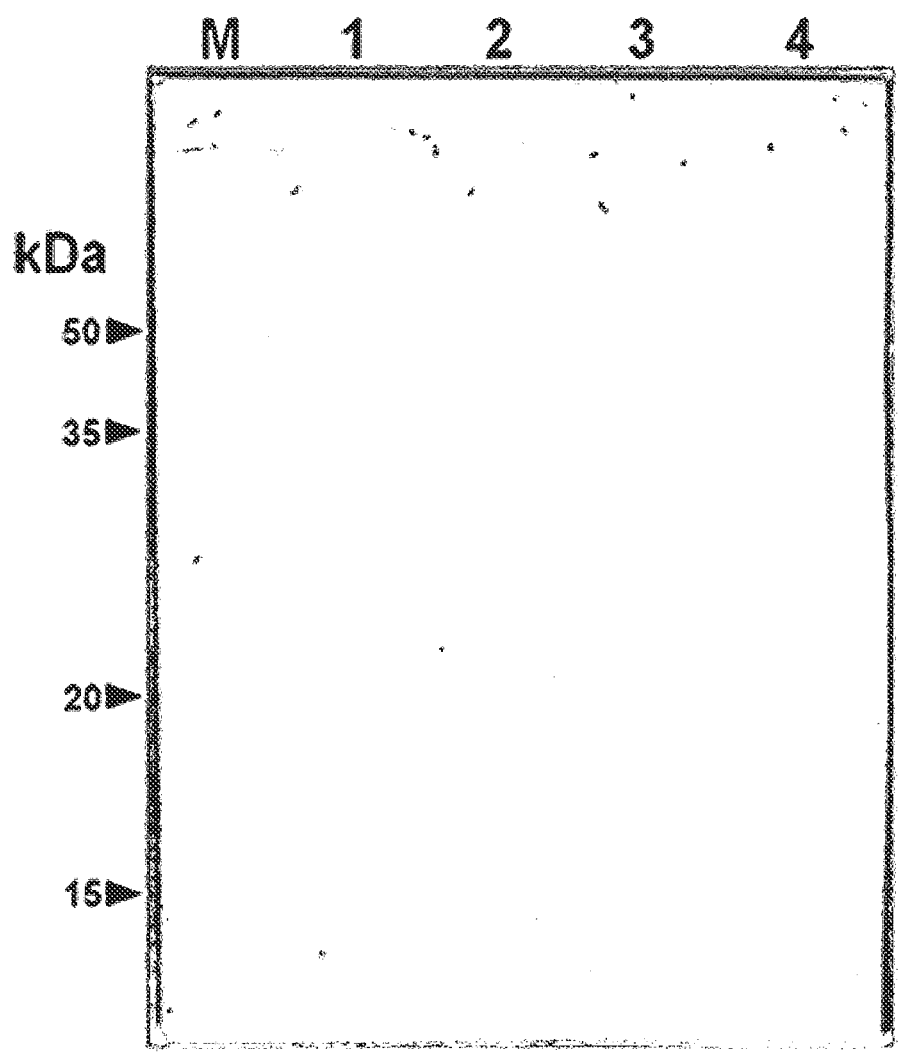
FIG. 11 shows the result of western blot assay using antibodies of AFP (1: native AY30 AFP; 2 and 3: recombinant AY30 AFP produced in a bacterial expression system; and 4: recombinant AY30 AFP produced in a *Pichia pastoris* expression system).

As a result, as show in FIG. 11, it was found from the western blot analysis that the recombinant AFP expressed in *P. pastoris* X33/Mut$^+$/pPICZαA-AY30 according to the present invention and the recombinant AFP expressed in bacteria have the same amino acid sequence as the native AFP.

Example 7

Analysis of Antifreeze Activity of AFP AY30

The changes in morphology of ice crystals by AFP AY30 were measured with a nanoliter osmometer (nanoliter osmometer, Otago Osmometers Ltd, New Zealand). Specifically, immersion oil was filled in a sample chamber, and the samples were floated on the oil. The sample chamber was placed on a stage and frozen quickly at −20° C. Then, the temperature was slowly increased such that most ice crystals were melted and the crystals to be observed were left. Thereafter, the temperature of the stage was slowly lowered to observe and measure the formation of ice crystals and the melting temperature. The freezing temperature, at which the ice crystals did not grow even when the temperature was lowered and were then rapidly grown, was measured to analysis the antifreeze activity (thermal hysteresis).

Figure 12:
Figure 13:
Figure 14:
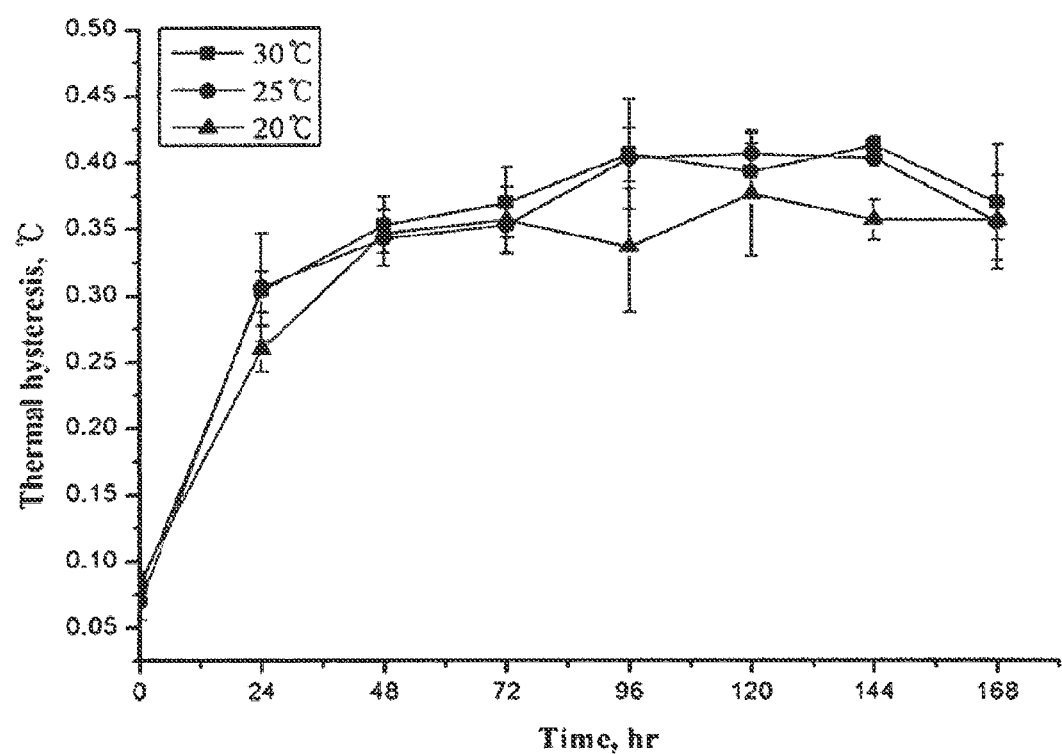
FIG. 14 is a graph showing the antifreeze activity under different culture temperature conditions.

As a result, as shown in the following table 1 and the graphs of FIGS. 12 to 14, it was found that the recombinant AY30 AFPs produced at different culture temperatures were the active forms having the antifreeze activity.

TABLE 1

| | 0 | 24 | 48 | 72 | 96 | 120 | 144 | 168 |
|---|---|---|---|---|---|---|---|---|
| 30° C. | 0.080 | 0.303 | 0.363 | 0.317 | 0.407 | 0.393 | 0.413 | 0.370 |
| 25° C. | 0.070 | 0.307 | 0.453 | 0.320 | 0.403 | 0.407 | 0.403 | 0.355 |

[Sequence Listing Free Text]

The nucleotide sequence of SEQ. ID. NO: 1 is a DNA sequence derived from *Leucosporidium* sp. AY30.

The invention claimed is:

1. A method for mass-producing an antifreeze protein derived from arctic yeast or a culture medium containing the same, comprising the steps of:
   (1) synthesizing a polynucleotide comprising the nucleotide sequence of SEQ. ID. NO: 1;
   (2) introducing the polynucleotide of step (1) into a *Pichia pastoris*-derived expression vector using an alcohol oxidase promoter (AOX1) to prepare a recombinant expression vector;
   (3) culturing a yeast transformant transformed with the recombinant expression vector; and
   (4) obtaining a culture medium from step (3).

2. The method of claim 1, wherein the *Pichia pastoris*-derived expression vector using the alcohol oxidase promoter (AOX1) in step (2) is pPICZαA.

3. The method of claim 1, wherein the recombinant expression vector in step (3) is pPICZαA-AY30 (Accession No.: KCTC 11917BP).

4. An isolated polynucleotide comprising the nucleotide sequence of SEQ. ID. NO: 1, expressing an antifreeze protein.

* * * * *